US012383251B2

(12) United States Patent
Bohl et al.

(10) Patent No.: US 12,383,251 B2
(45) Date of Patent: Aug. 12, 2025

(54) SYSTEMS AND METHODS FOR A SPINAL SHIELD FOR PROTECTING THE SPINAL CORD AND DURA DURING SURGICAL PROCEDURES

(71) Applicant: Dignity Health, San Francisco, CA (US)

(72) Inventors: Michael A. Bohl, San Francisco, CA (US); Randall Porter, San Francisco, CA (US); Udaya Kumar Kakarla, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 18/442,354

(22) Filed: Feb. 15, 2024

(65) Prior Publication Data

US 2024/0180543 A1 Jun. 6, 2024

Related U.S. Application Data

(62) Division of application No. 17/693,673, filed on Mar. 14, 2022, now Pat. No. 11,950,772, which is a division of application No. 16/625,195, filed as application No. PCT/US2018/039555 on Jun. 26, 2018, now abandoned.

(60) Provisional application No. 62/589,748, filed on Nov. 22, 2017, provisional application No. 62/537,068, filed on Jul. 26, 2017, provisional application No. 62/524,653, filed on Jun. 26, 2017.

(51) Int. Cl.
*A61B 17/02* (2006.01)

(52) U.S. Cl.
CPC .... *A61B 17/025* (2013.01); *A61B 2017/0262* (2013.01)

(58) Field of Classification Search
CPC .... A61B 2017/0262; A61B 2090/0815; A61B 17/7071; A61B 17/7043
See application file for complete search history.

(56) References Cited

U.S. PATENT DOCUMENTS

| | | | |
|---|---|---|---|
| 9,526,533 | B1 | 12/2016 | Aranibar et al. |
| 2002/0010466 | A1 | 1/2002 | Alleyne |
| 2005/0090899 | A1 | 4/2005 | DiPoto |
| 2005/0119657 | A1 | 6/2005 | Goldsmith |
| 2005/0177155 | A1 | 8/2005 | Alleyne |
| 2006/0264948 | A1 | 11/2006 | Williams |
| 2008/0262630 | A1 | 10/2008 | Fulmer et al. |
| 2009/0326592 | A1 | 12/2009 | Butler et al. |

(Continued)

FOREIGN PATENT DOCUMENTS

| | | |
|---|---|---|
| WO | 2015039104 A2 | 3/2015 |
| WO | 2017055929 A2 | 4/2017 |

OTHER PUBLICATIONS

European Patent Office, Extended European Search Report, Application No. 18822788.8, Mar. 5, 2021, 8 pages.

(Continued)

*Primary Examiner* — Samuel S Hanna
(74) *Attorney, Agent, or Firm* — Polsinelli PC

(57) ABSTRACT

Various embodiments of a spinal shield having a shield body including a plurality of lateral extensions configured to be positioned over an exposed spinal canal for establishing a protective barrier around the contents of the exposed spinal canal are disclosed.

3 Claims, 7 Drawing Sheets

100 110 102 118 116 116 114 112 104 116 108 116

100 116 116 115 112 115 102 118 104 110 108 115 114 115 116 116

(56) References Cited

U.S. PATENT DOCUMENTS

| | | | | |
|---|---|---|---|---|
| 2010/0174315 | A1 | 7/2010 | Scodary et al. | |
| 2010/0179597 | A1 | 7/2010 | Henderson et al. | |
| 2011/0125269 | A1* | 5/2011 | Moskowitz | A61F 2/4405 623/17.11 |
| 2011/0270397 | A1* | 11/2011 | Mac-Thiong | A61B 17/7071 623/17.11 |
| 2013/0123793 | A1 | 5/2013 | Kehres et al. | |
| 2016/0095632 | A1 | 4/2016 | Faulhaber | |
| 2022/0192646 | A1 | 6/2022 | Bohl et al. | |

OTHER PUBLICATIONS

Patent Cooperation Treaty, International Search Report and Written Opinion, International Application No. PCT/US2018/039555, Oct. 11, 2018, 12 pages.
European Patent Office, Communication pursuant to Article 94(3), Application No. 18822788.8, dated Feb. 15, 2023, 7 pages.
Canadian Intellectual Property Office, Office Action, Application No. 3,065,336, Jan. 24, 2024, 4 pages.

* cited by examiner

SYSTEMS AND METHODS FOR A SPINAL SHIELD FOR PROTECTING THE SPINAL CORD AND DURA DURING SURGICAL PROCEDURES

CROSS REFERENCE TO RELATED APPLICATIONS

This application is a divisional of U.S. application Ser. No. 17/693,673 filed on Mar. 14, 2022, which is a divisional of U.S. 371 National application Ser. No. 16/625,195 filed on Dec. 20, 2019, now abandoned, which is a 371 national of PCT International Application No. PCT/US2018/039555 filed on Jun. 26, 2018, which claims the benefit of U.S. Provisional Patent Application Serial Nos. 62/524,653 filed on Jun. 26, 2017; 62/537,068 filed on Jul. 26, 2017; and 62/589,748 filed on Nov. 22, 2017, which all are incorporated by reference in its entirety.

FIELD

The present disclosure generally relates to tools for protecting the spinal canal and its contents during medical procedures that require exposure of the spinal canal, and in particular to systems and methods for a spinal shield that protects the spinal cord and dura during surgical procedures.

BACKGROUND

A laminectomy procedure is employed to treat spine problems, including spinal stenosis, tumors, spinal deformities, and others. This procedure is sometimes referred to as a "spinal decompression surgery". In particular, during a laminectomy, a surgeon may remove the lamina and spinous process to provide access to the spinal canal, which, in turn, can create more space in the spinal canal and relieve pressure on the spinal canal contents.

Surgeons performing a laminectomy typically use rongeurs (bone cutting instrument), osteotomes (a bone chisel), ultra-sonic bone scalpels, and/or high-speed drills to perform laminectomies. After a laminectomy is performed, the contents of the spinal canal (including the dura, spinal cord, nerve roots, and blood vessels) are exposed and at risk to inadvertent injury during the rest of the surgical procedure. Examples of the types of injuries that can occur include dural tear, spinal cord injury, and nerve root injury. These injuries sometimes occur because of inadvertently dropped or mishandled surgical instruments (e.g., over the exposed spinal canal). Results of such mistakes can be mild to severe, and include repairable damage, such as a dural tear and spinal fluid leak, to unrepairable damage, such as spinal cord or nerve root injuries.

The types of surgical procedures that often take place after a laminectomy with the contents of the spinal canal exposed include, but are not limited to, cannulation of vertebral pedicles, placement of spinal fixation hardware (such as pedicle screws, fixating rods, and cap screws), decortication of bone, and placement of surgical drains. Past attempts to reduce the risk of injury to the contents of the spinal canal after a laminectomy have failed to produce a device that is sufficiently effective and easy to use to achieve wide adoption by surgeons.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
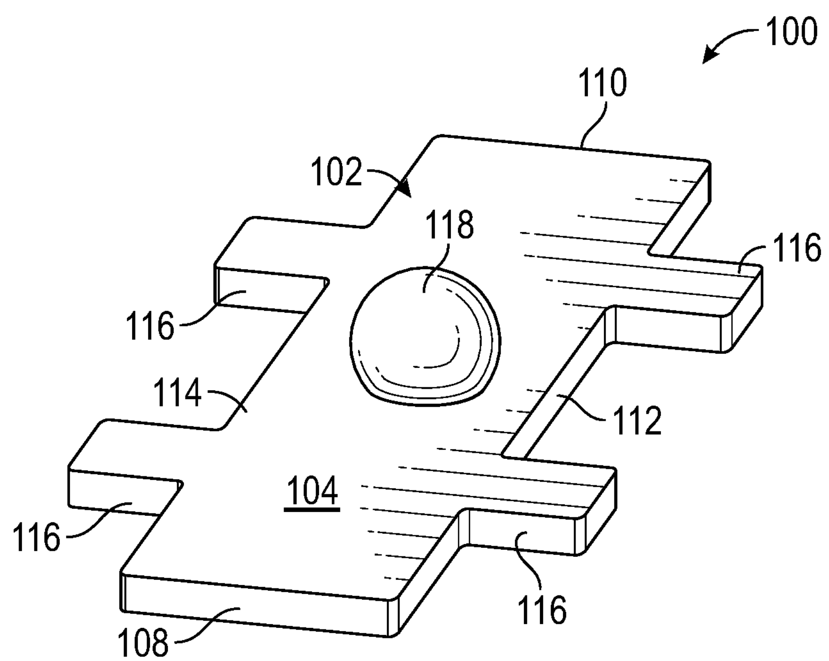
FIG. 1 is a perspective view of a first embodiment of a spinal shield, according to aspects of the present disclosure.

As noted above, a laminectomy is a common surgical procedure in which a portion of the posterior spinal column is removed to decompress the spinal cord and nerve roots. This is done to treat numerous spine diseases, including degenerative, infectious, neoplastic, traumatic, and congenital pathologies.

Instruments used after performing a laminectomy, once the contents of the spinal canal are exposed and vulnerable to injury, are highly varied, but typically include, screw drivers, drills, biting rongeurs, mallets, and osteotomes (bone chisels). During surgery, each of these conventional instruments pose a potential threat to the contents of the spinal canal (dura, spinal cord, nerve roots, and blood vessels) if such instruments are inadvertently dropped or mishandled.

Various embodiments of a spinal shield and related methods of use to protect the contents of the exposed spinal canal during a surgical procedure are disclosed herein. In one aspect, embodiments of the spinal shield are used to effectively protect the contents of the spinal canal during a surgical procedure, after a laminectomy has been performed, by establishing a protective structural barrier that surrounds the spinal canal and is configured to accommodate the contents of the spinal canal along various segments of the spinal column. In another aspect, embodiments of the spinal shield are configured to be easily inserted and removed from the surgical site by a surgeon by engaging a handle portion that extends outwardly from the shield body of the spinal shield. In some embodiments, the shield body defines a plurality of laterally extending legs configured to extend between access points for spinal fixation hardware inserted into the bone tissue after a laminectomy and to allow the shield body to rest above the spinal canal and establish a protective barrier around the spinal cord and dura. In some embodiments, the shield body defines a flat configuration, while in other embodiments of the spinal shield the shield body defines a semi-circular curved configuration. Referring to the drawings, embodiments of a spinal shield are illustrated and generally indicated as 100 and 200 in FIGS. 1-14.

As shown in FIGS. 1-5, a first embodiment of a spinal shield, designated 100, includes a rectangular-shaped shield body 102 having a generally planar configuration and can be generally configured to be placed over the spinal canal and dura of a patient to establish a protective barrier around the exposed spinal canal during a surgical procedure, such as a laminectomy. In some embodiments, the shield body 102 forms a top surface 104 and opposite bottom surface 106 that collectively define a front side 108, a rear side 110, a first lateral side 112, and an opposing second lateral side 114. As further shown, a plurality of lateral extensions 116 extend outwardly and/or downward from the first and second lateral sides 112, 114, respectively. The lateral extensions 116 permit the spinal shield 100 to be placed over the exposed spinal canal such that the lateral extensions 116 extend between the access points 9 to spinal fixation hardware. For example, the lateral extensions 116 may extend between spinal fixation hardware, such as pedicle screws 10 inserted within the access points 9 along both sides of the spinal column in a manner illustrated in FIG. 11. However, the present disclosure contemplates that other types of spinal fixation hardware may secured within access points 9.

In some embodiments, referring back to FIGS. 1-5, a handle portion 118 which acts as a handle may be defined along and extend outwardly from the top surface 104 of the shield body 102 and can be configured to permit a user, such as surgeon, to easily and securely grip the spinal shield 100 and position the shield body 102 over the exposed spinal canal during a surgical procedure as well as grip the shield body 102 again to remove the spinal shield 100 from its position over the spinal canal after surgery has been completed. In some embodiments, the handle portion 118 may have a spherical configuration, although in other embodiments the handle portion 118 may have a square configuration, a rectangular configuration, an asymmetrical configuration, and asymmetrical configuration shaped and sized to permit sure handling of the spinal shield 100 by the surgeon. In some embodiments, the handle portion 118 may be made from a flexible material rather than a rigid material that acts as a flexible tether configured for gripping by the surgeon. In some aspects, the shield body 102 may comprise one or more handle portions 118.

Figure 2:
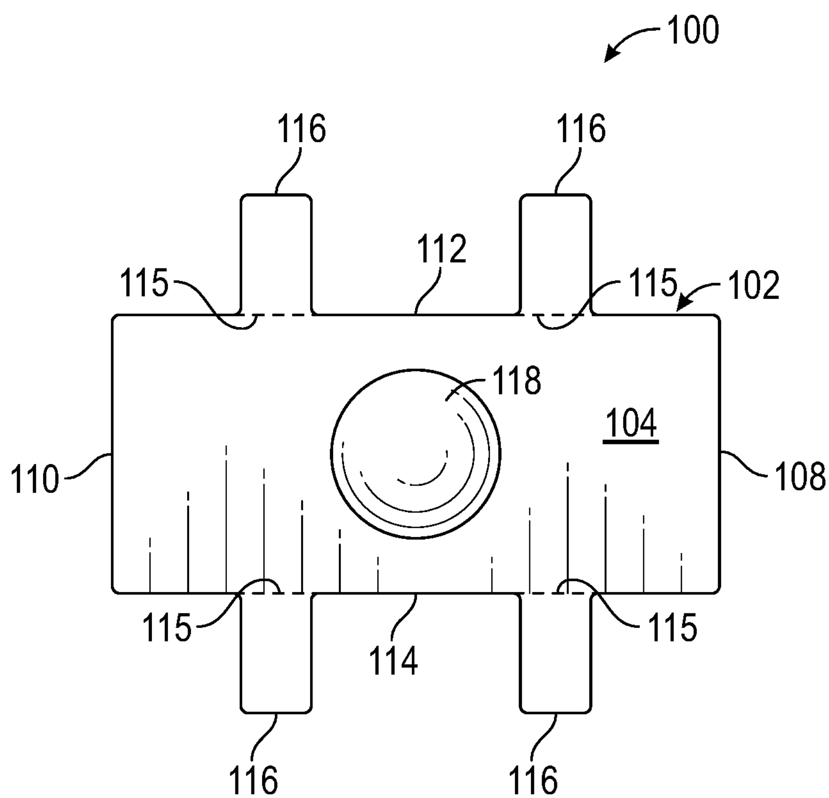
FIG. 2 is a top view of the spinal shield of FIG. 1, according to aspects of the present disclosure.
Figure 3:
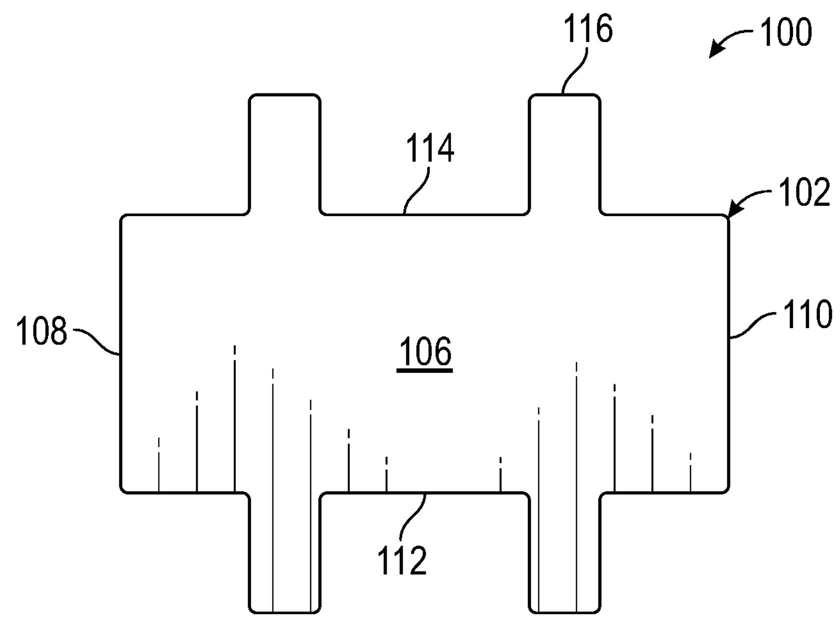
FIG. 3 is a bottom view of the spinal shield of FIG. 1, according to aspects of the present disclosure.
Figure 4:
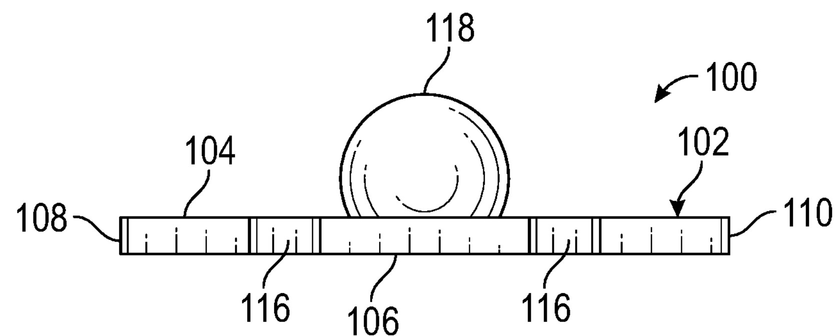
FIG. 4 is a side view of the spinal shield of FIG. 1, according to aspects of the present disclosure.
Figure 5:
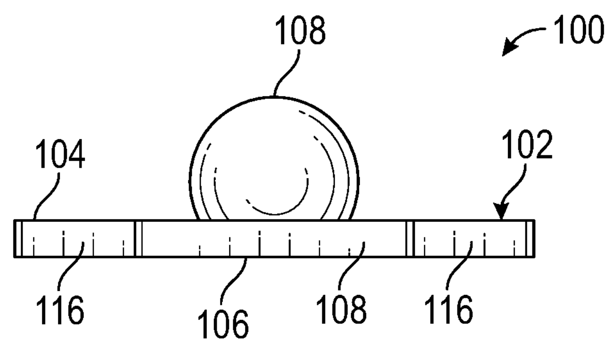
FIG. 5 is an end view of the spinal shield of FIG. 1, according to aspects of the present disclosure.
Figure 6:
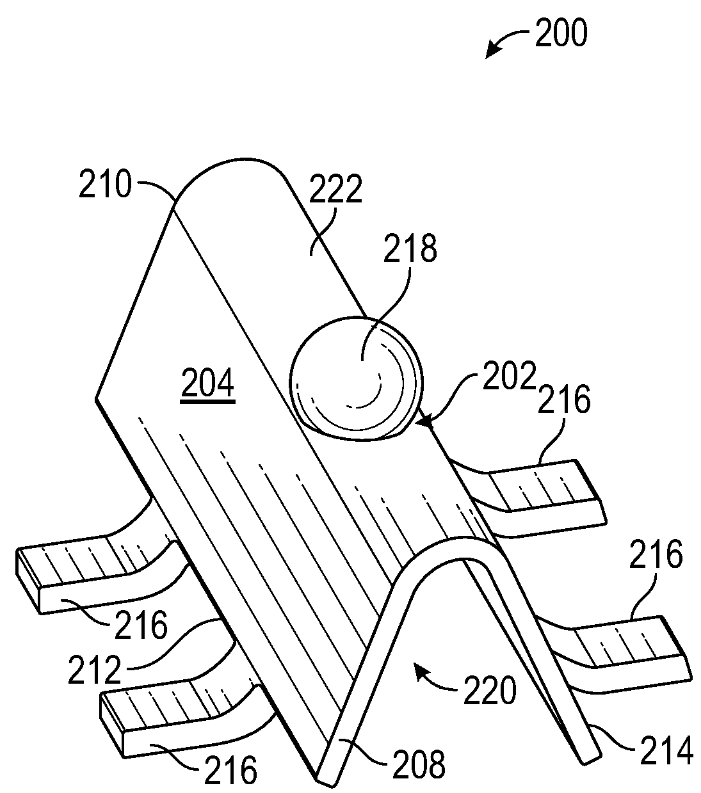
FIG. 6 is a perspective view of a second embodiment of the spinal shield, according to aspects of the present disclosure.
Figure 7:
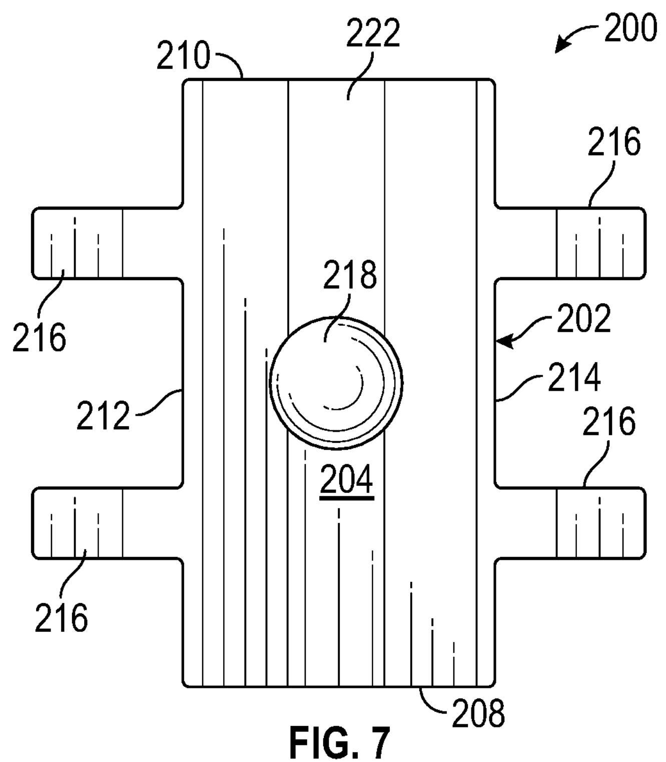
FIG. 7 is a top view of the spinal shield of FIG. 6, according to aspects of the present disclosure.

In some embodiments, the lateral extensions 116 may define a plurality of perforations 115 formed in a line parallel to the shield body 102 that allows each lateral extension 116 to be broken off from the shield body 102 when the spinal shield 100 is removed from the surgical site as shown in FIG. 2. Alternatively, the lateral extensions 116 do not include any perforations 115, but may be made of a frangible material that allows for breaking off the lateral extensions 116 using, for example, a bone cutting rongeur or other common surgical instrument, to enable easier removal of the spinal shield 100 from the surgical site after spinal fixation hardware has been placed.

Figure 14:
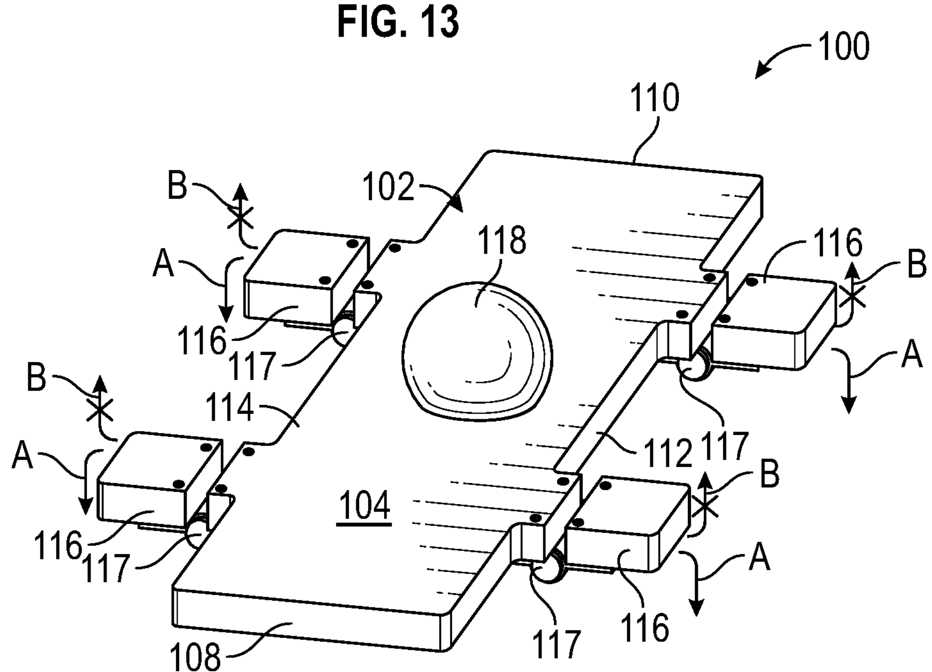
FIG. 14 is a perspective view showing the first embodiment of the spinal shield having hinges that allow the lateral extensions to only rotate in a downward direction, according to aspects of the present disclosure.

Referring to FIG. 14, in some embodiments each of the lateral extensions 116 of the shield body 102 may include a hinge 117 that allows each respective lateral extension 116 to bias or rotate in a downward direction A only and is prevented from biasing or rotating in an opposite upward direction B so that the spinal shield 100 can be more easily removed from the surgical site following placement of the spinal fixation hardware.

Figure 11:
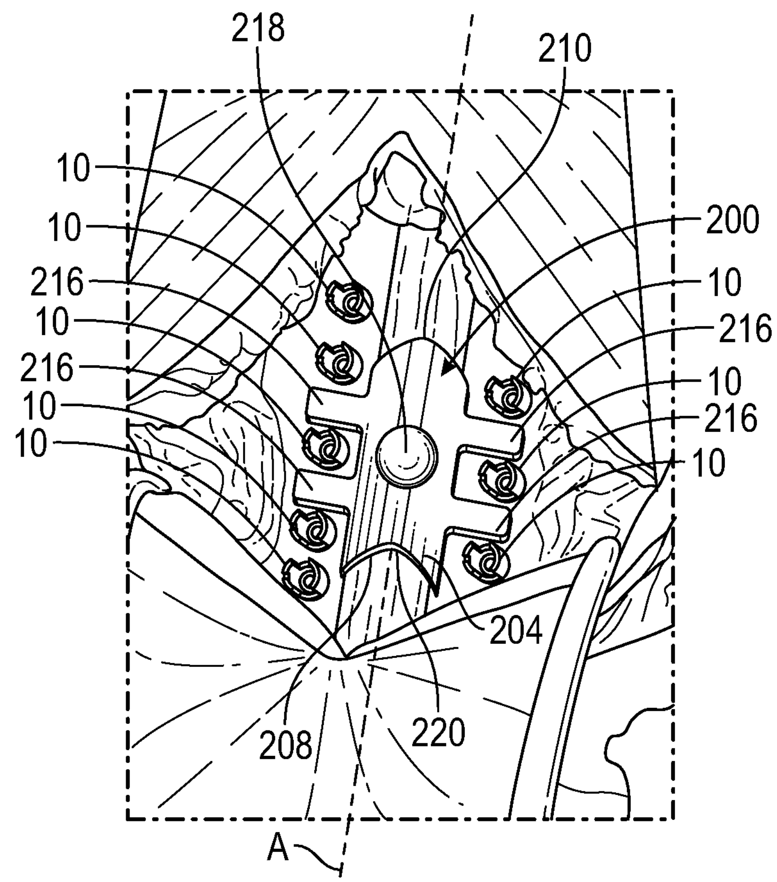
FIG. 11 is an illustration showing placement of the spinal shield along the spinal canal, according to aspects of the present disclosure.

Referring to FIGS. 6-10, a second embodiment of the spinal shield, designated 200, includes a generally arc-shaped/arcuate shield body 202 having a semi-circular configuration and is shaped and sized to be placed over the spinal canal and dura of a patient to establish a protective barrier around the exposed spinal canal during a surgical procedure, such as a laminectomy. In some embodiments, the shield body 202 forms a top surface 204 and an opposite bottom surface 206 that collectively define a front side 208, a rear side 210, a first lateral side 212, and an opposite second lateral side 214. As shown, the shield body 202 defines an open channel 220 formed between the first lateral side 212 and the opposing second lateral side 214 that provides an open area between the bottom side 206 of the shield body 202 and the exposed spinal canal as illustrated in FIG. 11. As shown, the top surface 204 forms an apex 222 that extends along the longitudinal axis of the shield body 202. The configuration of the open channel 220 allows the spinal shield 200 to be positioned above and across the exposed spinal canal such that neither the bottom side 206 nor the first and second lateral sides 212 and 214 of the shield body 202 directly contact the exposed spinal canal and its contents.

As further shown, a plurality of laterally extending legs 216 extend at an angle outwardly and/or downward from the first and second lateral sides 212, 214, respectively, of the shield body 202 and are configured to position the spinal shield 200 above and across the exposed spinal canal. In this configuration, the plurality of laterally extending legs 216 will rest on opposing sides of the exposed spinal canal and between each set of access points 9 in which the pedicle screws 10 are secured therein along either side of the exposed spinal canal in a manner illustrated in FIG. 11.

In some embodiments, the laterally extending legs 216 may have a plurality of perforations formed in a line for that allows each laterally extending leg 216 to be broken off from the shield body 202 when the spinal shield is removed from the surgical site. Alternatively, the lateral extensions 216 do not include a perforated segment but may be made of a material that allows for breaking off the lateral extensions 216 using, for example, a bone cutting rongeur or other common surgical instrument, to enable easier removal of the spinal shield 100 from the surgical site after spinal fixation hardware has been placed.

Figure 13:
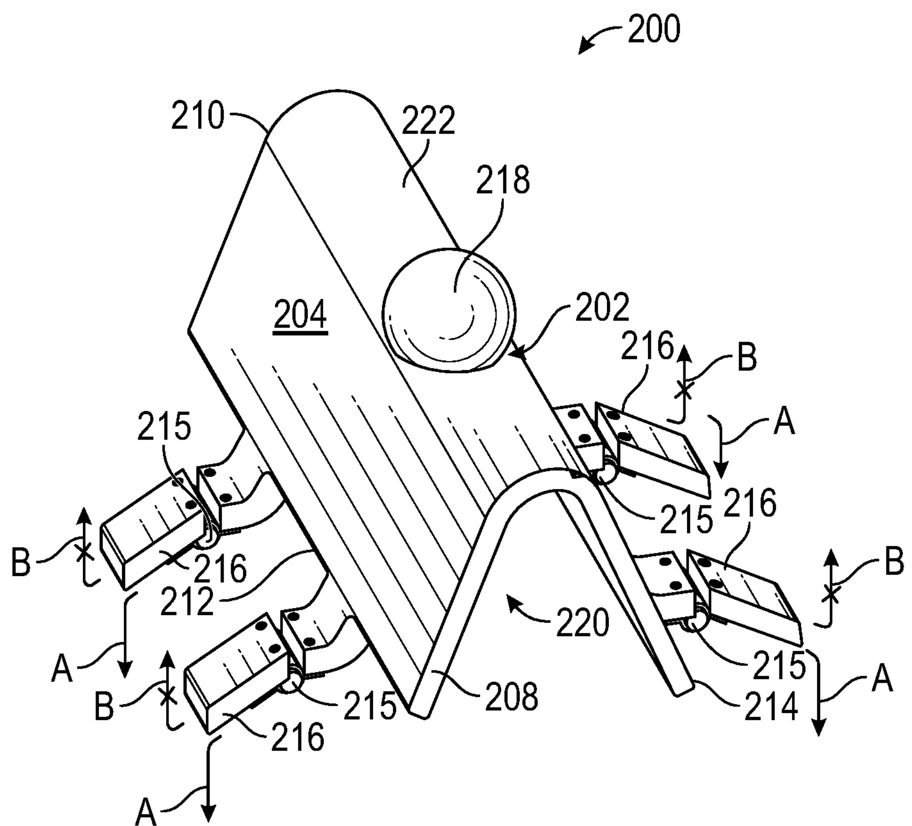
FIG. 13 is a perspective view showing the second embodiment of the spinal shield having hinges that allow the laterally extending legs to only rotate in a downward direction, according to aspects of the present disclosure.

Referring to FIG. 13, in some embodiments each of the laterally extending legs 216 of the shield body 202 may include a hinge 215 that allows each respective laterally extending leg 216 to bias or rotate in a downward direction A only and is prevented from biasing or rotating in an opposite upward direction B so that the spinal shield 100 can be more easily removed from the surgical site following placement of the spinal fixation hardware.

In some embodiments, a handle portion 218 may act as a handle defined along and extend outwardly relative to the top surface 204 and is configured to permit a user, such as surgeon, to easily grip the spinal shield 200 and position the shield body 202 over the exposed spinal canal during a surgical procedure as well as easily grip the shield body 202 again to remove the spinal shield 200 from its position over the exposed spinal canal after surgery has been completed. In some embodiments, the handle portion 218 may have a spherical configuration, although in other embodiments the handle portion 218 may have a square configuration, a rectangular configuration, an asymmetrical configuration, and asymmetrical configuration shaped and sized to permit sure handling of the spinal shield 200 by the surgeon. In some aspects, the shield body 202 may include a plurality of handle portions 218.

Referring back to FIG. 11, the spinal shield 200 is shown positioned above and along the longitudinal axis A of the exposed spinal canal such that the laterally extending legs 216 extend laterally on both sides of the exposed spinal canal and rest between each pair of spinal fixation screws 10 secured to either side of the spinal canal. During a surgical procedure, such as a laminectomy, the spinal shield 200 is placed over the exposed spinal canal by the surgeon to establish a protective structural barrier around the exposed spinal canal without contacting the spinal fixation hardware 10.

Figure 12:
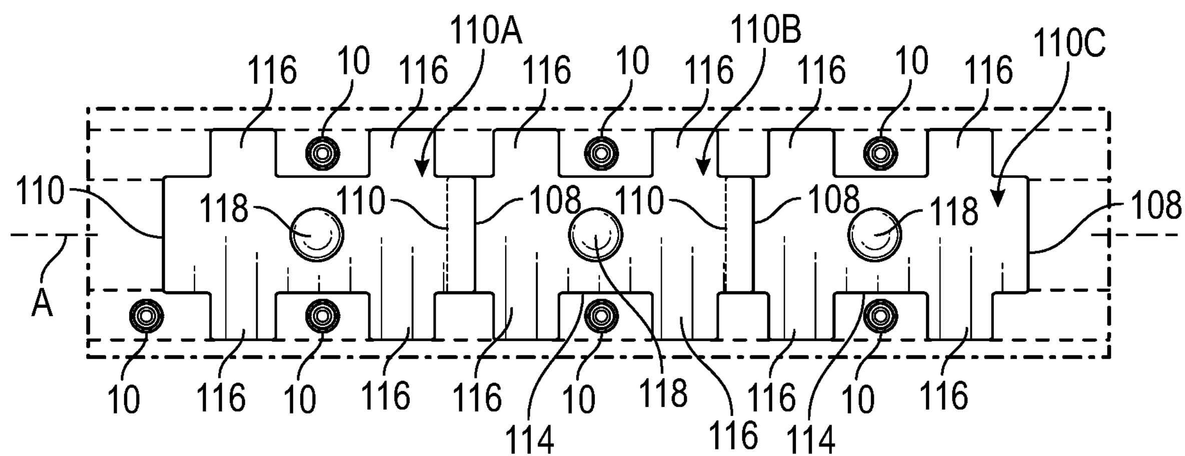
FIG. 12 is an illustration showing a plurality of spinal shields arranged in series along the spinal canal during surgery, according to aspects of the present disclosure.

Referring to FIG. 12, a plurality of spinal shields 100 (or spinal shields 200) may be aligned in series along the longitudinal axis A of the exposed spinal canal such that the entire length of the exposed spinal canal is protected. As shown, each of the spinal shields 100 may overlap one another in series; however, alternatively, the spinal shields 100 (or spinal shields 200) may directly contact each other end-to-end in series rather than overlap.

In one aspect, spinal shields 100 and 200 may be made from materials that provide substantial structural integrity and rigidity to protect the underlying tissue or muscle from unwanted exposure to physical and chemical elements. For example, in some embodiments spinal shields 100 and 200 may be manufactured or comprised of any number of suitable sterilizable or nonsterilizable materials, such as a metallic material, resin, ceramic, polymer, alloy, biodegradable composite, bioactive material, or any combination thereof. In some embodiments, the surface area of the spinal shields 100 and 200 may be coated with any number of suitable materials to provide, for example, antibacterial properties.

In some embodiments, the spinal shields 100 and 200 may be made of material(s) that make the shield body 102 or 202 substantially flexible to accommodate changes in a patient's physiology. For example, the spinal shields 100 and 200 may be positioned around portions of the patient's body to protected, such as the spine as discussed herein.

Figure 8:
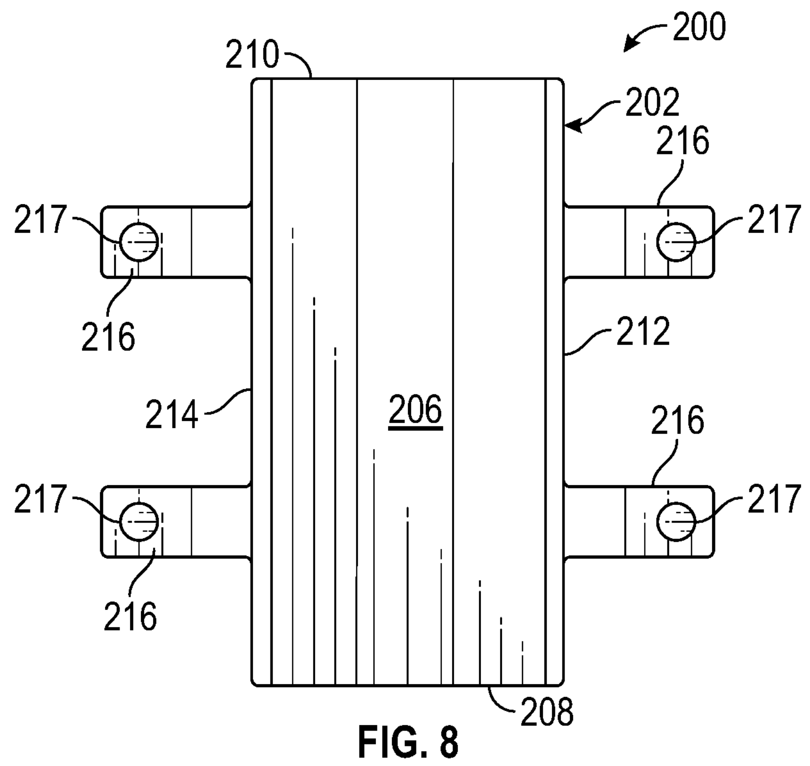
FIG. 8 is a bottom view of the spinal shield of FIG. 6, according to aspects of the present disclosure.
Figure 9:
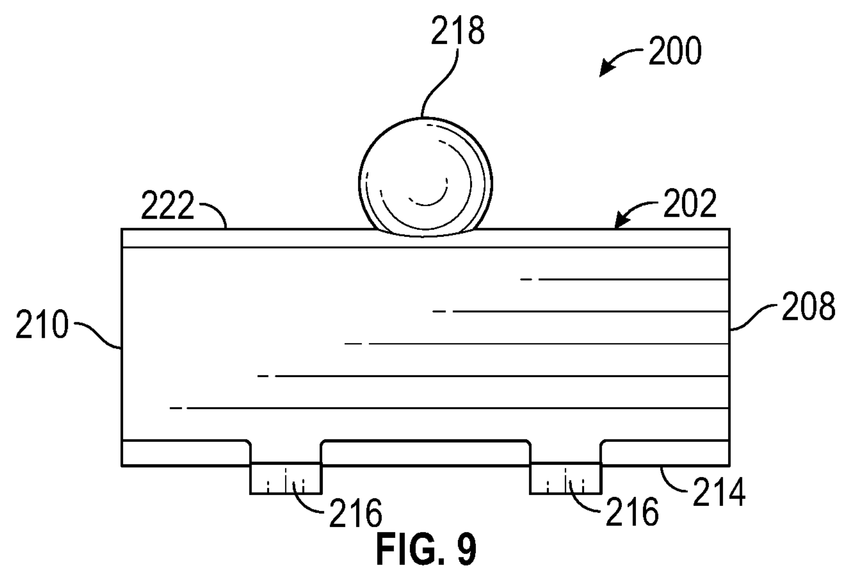
FIG. 9 is a side view of the spinal shield of FIG. 6, according to aspects of the present disclosure.
Figure 10:
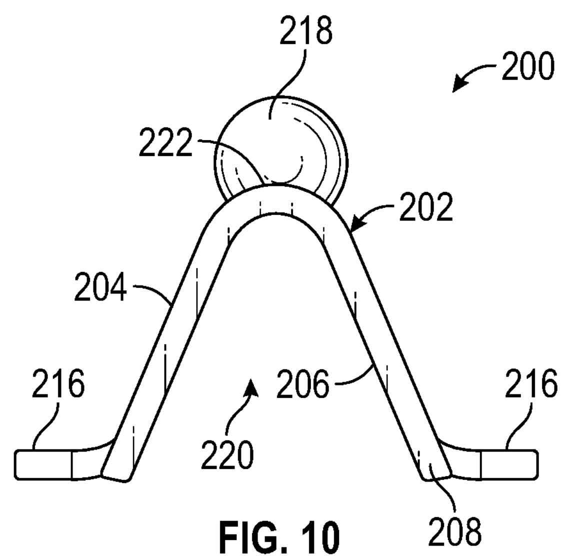
FIG. 10 is an end view of the spinal shield of FIG. 6, according to aspects of the present disclosure.

In some embodiments, the spinal shields 100 and 200 may have one or more support pads 217 attached to the underside of each lateral extension 116 or laterally extending leg 216. By way of example as shown in FIG. 8, a respective support pad 217 may be attached to the underside of each laterally extending leg 216 to reduce or eliminate unwanted movement of the shield body 202 as well as prevent pressing, bumping, or irritation by the spinal shield 200 after placement. In some embodiments, the support pads 217 may have a variety of shapes or configurations, including, but not limited to a square configuration, a rectangular configuration, a circular configuration, an oval configuration or any other shaped suitable for attachment to the underside of either the laterally extending legs 216 or lateral extensions 116. In some embodiments, the support pads 217 may be coated with an adhesive to assist in fixing the position of the spinal shields 100 and 200 and to further prevent unwanted movement after placement. In some embodiments, the support pads 217 may have a textured surface that allows the spinal shields 100 and 200 to remain in the correct position via the coefficient of friction after placement by the surgeon along the surgical site.

In some embodiments, the entire spinal shields 100 and 200 or portions thereof may define channels, ridges, protrusions, or any combination thereof formed along the shield body 102 or shield body 202 for interacting with the patient's skin and muscle tissue as well as enhancing the gripping capacity of the spinal shields 100 and 200. In addition, these features may be dispersed across various portions of the shield body 102 or 202 in any known configuration that aligns with the preference of the user. Moreover, these features may be advantageous for interacting or diverting the flow of liquid over the spinal bodies 102 and 202.

In one method of manufacture, the spinal shields 100 and 200 may be manufactured using 3D printing methods by printing and connecting various discrete components (e.g., shield body, handle portion, etc.) together to assemble the spinal shields 100 and 200, or alternatively, by unitary construction through injection molding processes. One non-limiting example of a 3D printing method that may be used to manufacture the spinal shields 100 and 200 are disclosed in PCT patent application serial number PCT/US2018/035223 entitled Synthetic Spine, filed on May 30, 2018, and is herein incorporated by reference in its entirety. In some embodiments, the spinal shields 100 and 200 may be manufactured such that any interior portion thereof is hollow (not shown). For example, the lateral extensions 116 or laterally extending legs 216 may have a hollow interior (not shown), while the shield body 102 or 202 may have a substantially solid configuration, or vice versa, or alternatively, both the shield body 102 and 202 and the lateral extensions 116 or laterally extending legs 216 are of a hollow construction.

In some embodiments, the spinal shields 100 and 200 may be made of a substantially transparent material, such as a transparent medical grade polymer in which the user may see through the device and observe the patient's anatomy beneath. Alternatively, the spinal shields 100 and 200 may be made of a substantially translucent material.

In some embodiments, the spinal shields 100 and 200 may be fitted with one or more magnifying devices having a lens arrangement that provides a magnified view of the surgical site.

In some embodiments, a plurality of spinal shields 100 and 200 may be connected together by mechanical components, such as a locking pin, gripping jaws, tethering, texture surfaces, latches, or any combination thereof. In addition, the spinal shields 100 and 200 may be connected to one another using adhesives, fusing, magnets, or any chemical or non-chemical bonding methods. In some embodiments, the spinal shields 100 and 200 may be constructed such that the anterior, posterior, or both ends define a sloped edge configuration (not shown) such that one spinal shield 100 and 200 may slide over the slop edge configuration of another spinal shield 100 and 200.

In some embodiments, the spinal shields 100 and 200 may include a coupling device or adhesive (not shown) such that the spinal shields 100 and 200 may be temporarily affixed to a patient's anatomy during the duration of a surgery. For example, the spinal shields 100 and 200 may be surgically tethered, fused, fixed, glued, latched, otherwise coupled to or any combination thereof, to the patient's anatomy. In addition, it is contemplated that this fastening method could be used to fasten the spinal shields 100 and 200 to other external components. For example, the spinal shields 100 and 200 may be fastened to a structural rig disposed around a portion of the patient's anatomy.

In some embodiments, the spinal shields 100 and 200 may include lateral extensions 116 of spinal shield 100 or laterally extending legs 216 of spinal shield 200 that cannot be broken off as in the embodiment described above. It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of establishing a protective barrier around a surgical site comprising: providing a first spinal shield comprising:

a shield body forming a top side, a bottom side that collectively define a front side, a rear side, a first lateral side, and a second lateral side opposite the first lateral side, wherein the shield body defines a flat configuration;

a plurality of lateral extensions that extend outwardly from the first and second lateral sides, respectively; and a handle portion that extends outwardly from the shield body in perpendicular relation to the shield body;

grasping the handle portion of the first spinal shield; and placing the first spinal shield in a position over the exposed surgical site;

wherein each of the plurality of laterally extending legs defines one or more perforations such that each of the plurality of laterally extending legs is broken off along the one or more perforations when removing the spinal shield from the exposed surgical site.

2. The method of claim 1, further comprising:

placing a second spinal shield in a position adjacent to the first spinal shield.

3. A method of establishing a protective barrier around a surgical site comprising:

providing a first spinal shield comprising:

a shield body forming a top side, a bottom side that collectively define a front side, a rear side, a first lateral side, and a second lateral side opposite the first lateral side, wherein the shield body defines a flat configuration;

a plurality of lateral extensions that extend outwardly from the first and second lateral sides, respectively; and a handle portion that extends outwardly from the shield body in perpendicular relation to the shield body;

grasping the handle portion of the first spinal shield; and placing the first spinal shield in a position over the exposed surgical site;

wherein each of the plurality of laterally extending legs is made of a frangible material such that each of the plurality of laterally extending legs is broken off from the shield body when removing the spinal shield from the exposed surgical site.

* * * * *